(12) United States Patent
Singh

(10) Patent No.: US 11,413,194 B2
(45) Date of Patent: Aug. 16, 2022

(54) PROTECTIVE FACE COVERING

(71) Applicant: INDUSTRIAL HYGIENE CONSULTANTS, INC., Montclair, NJ (US)

(72) Inventor: Uday Singh, Bloomfield, NJ (US)

(73) Assignee: Industrial Hygiene Consultants, Inc., Montclair, NJ (US)

( * ) Notice: Subject to any disclaimer, the term of this patent is extended or adjusted under 35 U.S.C. 154(b) by 373 days.

(21) Appl. No.: 15/869,621

(22) Filed: Jan. 12, 2018

(65) Prior Publication Data

US 2018/0193201 A1 Jul. 12, 2018

Related U.S. Application Data

(60) Provisional application No. 62/445,407, filed on Jan. 12, 2017.

(51) Int. Cl.
| | |
|---|---|
| *A61F 13/12* | (2006.01) |
| *A41D 13/11* | (2006.01) |
| *A61F 15/00* | (2006.01) |
| *A61M 16/10* | (2006.01) |
| *A62B 23/06* | (2006.01) |
| *A61M 15/08* | (2006.01) |

(52) U.S. Cl.
CPC ........ *A61F 13/126* (2013.01); *A41D 13/1176* (2013.01); *A61F 13/122* (2013.01); *A61F 15/001* (2013.01); *A61M 16/107* (2014.02); *A61M 16/1075* (2013.01); *A62B 23/06* (2013.01); *A61M 15/085* (2014.02); *A61M 16/1045* (2013.01)

(58) Field of Classification Search
CPC .... A61F 13/126; A61F 13/122; A61F 15/001; A61M 16/107; A61M 16/1075; A61M 15/085; A61M 16/1045; A61M 16/0688; A61M 2205/0216; A61B 5/6819; A61B 5/682; A62B 18/00; A62B 18/02; A62B 18/025; A62B 18/08; A62B 23/06; A41D 13/1176; A41D 13/1138; A41D 13/11; A61K 8/0208; A61K 8/0212
USPC ................... 128/858, 206.14, 206.18, 206.12
See application file for complete search history.

(56) References Cited

U.S. PATENT DOCUMENTS

| | | | | | |
|---|---|---|---|---|---|
| 3,802,426 | A | * | 4/1974 | Sakamoto | A62B 23/06 128/206.11 |
| 4,240,420 | A | * | 12/1980 | Riaboy | A62B 23/06 55/DIG. 35 |
| 4,354,489 | A | * | 10/1982 | Riaboy | A41D 13/1176 128/206.14 |
| 4,534,342 | A | * | 8/1985 | Pexa | A61F 13/126 602/74 |
| 4,984,302 | A | * | 1/1991 | Lincoln | A41D 13/1176 2/206 |

(Continued)

*Primary Examiner* — Erin Deery
*Assistant Examiner* — Robin Han

(57) ABSTRACT

Disclosed herein are facial covering that are configured to be placed on facial skin and that may be placed on the skin in a sealed relationship such that air leakage is minimized. The covering may include a member configured to fit flush against skin surrounding at least one of nasal air passages and a mouth of a user, the member including at least one aperture to permit breathing through the nasal air passages, the member being configured to adhere to the skin; and filter material positioned within a space defined by the at least one aperture.

15 Claims, 4 Drawing Sheets

(56) References Cited

U.S. PATENT DOCUMENTS

| | | | | |
|---|---|---|---|---|
| 6,206,902 B1* | 3/2001 | Morikane | ............. | A61Q 19/00 |
| | | | | 602/41 |
| 2009/0277451 A1* | 11/2009 | Weinberg | ........... | A41D 13/1176 |
| | | | | 128/206.14 |
| 2010/0258130 A1* | 10/2010 | Wu | .................... | A41D 13/1107 |
| | | | | 128/206.13 |
| 2016/0037836 A1* | 2/2016 | Tuan | .................... | A62B 23/025 |
| | | | | 128/863 |

\* cited by examiner

PROTECTIVE FACE COVERING

CROSS REFERENCE TO RELATED APPLICATIONS

This application claims the benefit of U.S. Provisional Application Ser. No. 62/445,407 filed on Jan. 12, 2017, the entire contents of which are hereby incorporated by reference.

FIGURE SELECTED FOR PUBLICATION

FIG. 3

BACKGROUND

Technical Field

The present disclosure relates generally to a covering to protect an area of skin, and more particularly to an aesthetically pleasing covering for protecting otherwise exposed nasal and/or other facial surfaces.

Description of the Related Art

People tend to be prone to respiratory illnesses during the winter months. Scientists postulate that viruses which include an outer layer that are normally liquid in warm conditions harden into a protective rubbery coat when chilled. When the weather is warmer than 60 degrees F., viruses have difficulty surviving when travelling through air. The cold, hardened protective rubbery coat of the pathogen increases the pathogens chances of survival. When the pathogen enters the body, the body heat melts the toughened viral coat and when back in the liquid phase is capable of infecting cells.

Moreover, cold air is known to provoke respiratory symptoms of people who suffer from respiratory illness such as, for example, asthma. While the effect of cold air on the skin is mainly cooling, the effect on the airways is cooling and drying. When an individual is exercising, e.g., running outside, the skin tends to sweat. The resulting moisture of the skin causes the skin to cool more rapidly. When the skin around or near the airways is cooled, the air that is breathed tends to cool and dry the airways more rapidly. For an adequately clothed person, only the skin of the face is exposed to the cold air. During heavy exercise in cold weather conditions, the facial skin, nasal mucosa, oral mucosa, pharynx, larynx, and lower airways are possible trigger sites for cold air-provoked respiratory symptoms. The short term response for nasal breathing of cold air may include congestion and sneezing. Such respiratory responses for facial skin cooling may include bronchoconstriction, which makes breathing challenging. Even if the effects of the cold air are short term and do not result in illness, the cold air may effectively preclude a person from exercising in such weather at least because heavy breathing is difficult when the airways tighten in response to the cold air.

Furthermore, conventional masks that are not in direct, sealed contacting relationship with the skin are prone to have the problem of mask fogging in which eyewear collects condensation. Mask fogging results from warm, humid air from the breath of a user meeting a cooler surface. since warmer air is capable of holding more water vapor (water in gas form) than cooler air. As the warmer air seeps out from under the mask, the warmer air comes into contact with the colder eyewear, thereby causes the lenses of the eyewear to fog.

Accordingly, there is a need for a device that would inhibit the skin surrounding the airways from cooling and/or that would inhibit the entry of pathogens into the airways, particularly in cold weather conditions.

SUMMARY

The present disclosure relates generally to a covering to protect an area of skin, and more particularly to an aesthetically pleasing covering for protecting otherwise exposed nasal and/or other facial surfaces. In particular, facial coverings are disclosed herein that are configured to be placed on facial skin and that may be placed on the skin in a sealed relationship such that air leakage is minimized A facial covering may be configured to be placed on facial skin. The covering may include a member configured to fit flush against skin surrounding at least one of nasal air passages and a mouth of a user, the member including at least one aperture to permit breathing through the nasal air passages, the member being configured to adhere to the skin; and filter material positioned within a space defined by the at least one aperture.

A facial covering configured to be placed on facial skin may include a first member configured to fit flush against skin surrounding at least one of nasal air passages of a user, the first member including at least one aperture to permit breathing through the nasal air passages, the first member being configured to adhere to the skin; a fibrous material disposed within the at least one aperture, the fibrous material including a plurality of filaments configured to trap foreign particles and to warm air entering into the at least one aperture. The fibrous material may be secured to the first member. The facial covering may further include a second member configured to be secured around a mouth of the user, the second member being outwardly curved. The first member may include an adhesive backing and the second member may include an adhesive backing. The fibrous material may be a fabric. The filaments may be clustered together to have a density that warms and filters substances in the air entering into the at least one aperture. The first and second members may form a unitary structure.

A kit may include at least one of the protective coverings and a means to secure the protective coverings to the skin of a user. For example, the kit may include an adhesive tape such as double-sided tape.

The above and other aspects, features and advantages of the present invention will become apparent from the following description read in conjunction with the accompanying drawings, in which like reference numerals designate the same elements.

BRIEF DESCRIPTION OF THE DRAWINGS

A further understanding of the present invention can be obtained by reference to a preferred embodiment set forth in the illustrations of the accompanying drawings. Although the illustrated preferred embodiment is merely exemplary of methods, structures and compositions for carrying out the present invention, both the organization and method of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which.

DETAILED DESCRIPTION OF THE PREFERRED EMBODIMENTS

Figure 1:
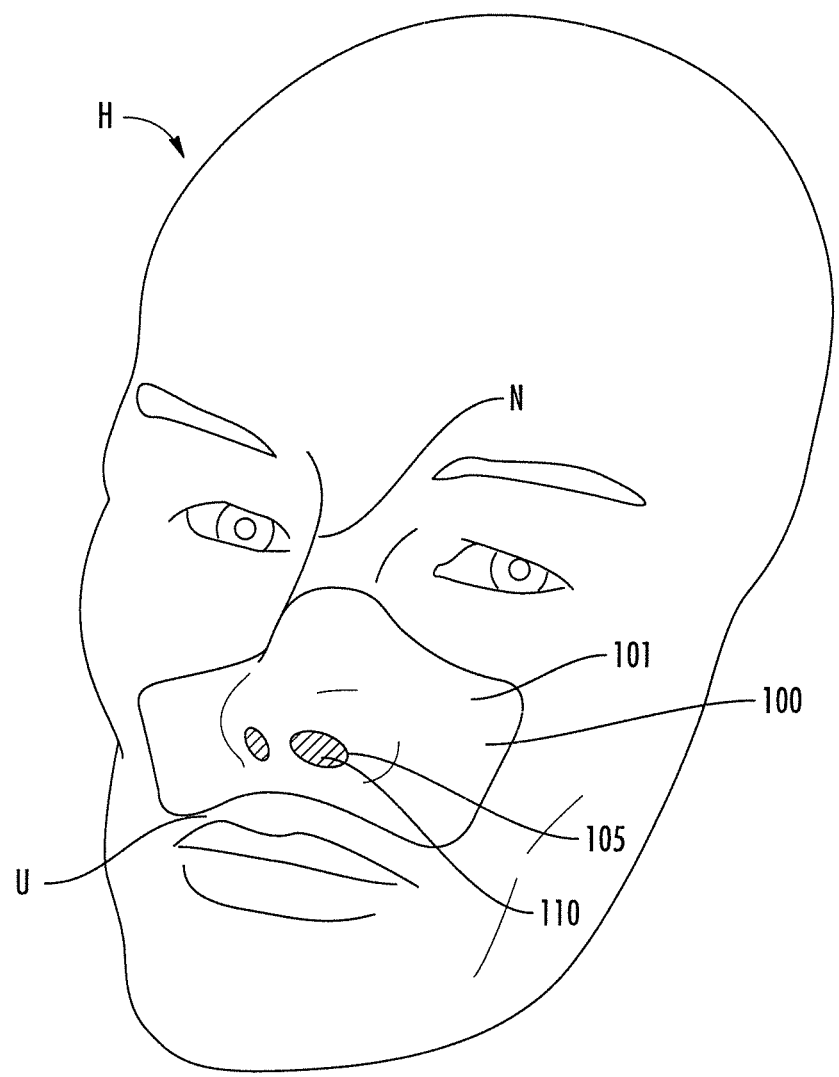
FIG. 1 is a perspective view of a facial protective covering shown relative to a human face in accordance with an embodiment the present disclosure.
Figure 2:
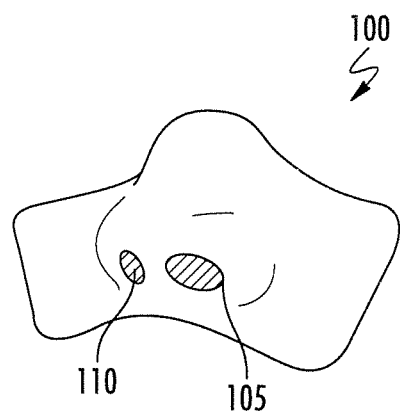
FIG. 2 is a perspective view of the facial protective covering of FIG. 1.

As required, a detailed illustrative embodiment of the present invention is disclosed herein. However, techniques, systems, compositions and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the invention in any manner.

As shown in FIG. 1, a facial covering 100 is secured atop a nose N of a head H of a person. The facial covering 100 may be formed of a plastic or a latex or a polyurethane material and is configured to make a sealing contact with the skin. In particular, the facial covering 100 may be adhered to the skin via glue or a tape (e.g., double stick tape) such that the facial covering 100 is brought into a close, sealing contact with the skin. The material forming forming the facial covering 100 may be generally clear such that when placed onto the skin pf the face, it may be aesthetically pleasing and may permit the skin underneath the covering to remain visible. Alternatively, an exterior surface 101 of a material, such as a fabric, may be secured to the outwardly facing surface of the facial covering 100. The material forming the exterior surface 101 may be a fabric or textile having a pattern, for example.

The facial covering 100 may include apertures 105 for each of the nasal openings. These apertures 105 permit the wearer to continue breathing through the nose even though the skin near the nasal openings is covered. A filter material 110 may cover the apertures 105. The filter material 110 may be formed, for example, from a gauze and/or cotton material. The filter material 110 may capture fine particles in the air being breathed and/or warm the air that is inhaled through the nostrils. When only wearing facial covering 100, it may be desirable for the wearer to breathe through his nose and to keep his mouth closed so that the cold air is not breathed in through the mouth. However, the facial covering 100 may be shaped so as to extend down from the nose N toward the mouth and/or toward or around the chin without covering the mouth itself such that the skin around the mouth may also be substantially covered and not directly exposed to cold air. As the facial covering 100 may be formed from a substantially flexible material, the normal functioning and movement of the mouth and the face may continue unimpaired by the wearing of the facial covering 100.

The facial covering 100 is configured to fit flush against a wearer or user's skin in a sealed relationship. To accomplish this, the facial covering 100 may be custom molded to fit the wearer's face. A kit may include a plaster material that is to be placed on the wearer's face to form a mold. When removed from the wearer's face, the resultant cast can be used to provide a surface on which a liquid latex or the like can be placed such that when it hardens a perfectly molded latex or the like covering is formed. Alternatively, the facial covering 100 may be provided in a variety of common sizes and shapes corresponding to a variety of facial shapes (e.g., narrow nose, wide nose, etc.)

Figure 3:
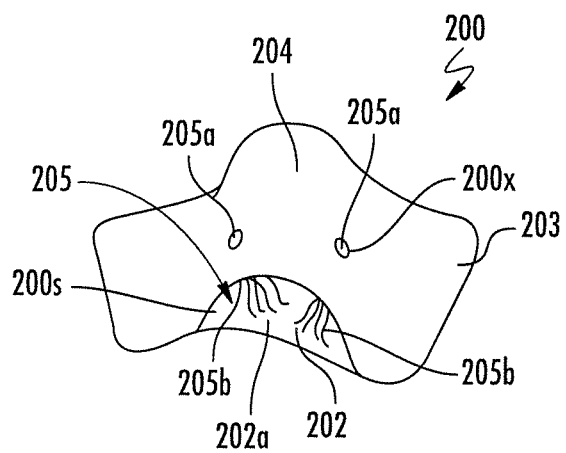
FIG. 3 is a perspective view of a facial protective covering in accordance with another embodiment of the present disclosure.

With reference to FIG. 3, a facial covering 200 according to another embodiment of the present disclosure will now be described. The facial covering 200 may include a first layer 202 that may be formed, for example, from a latex or polyurethane material which may be secured or adhered to a second layer 203 that may be formed from a fabric or textile material, for example. The first layer 202 is configured to be adhered to a skin of a user's face, for example, by using glue or tape (e.g., double stick tape). The facial covering 200 may include a nose ridge 204 that is configured to approximate the shape of the user's nose. A portion 202a of the first layer 202 may be separated from the second layer 203 such that the portion 202a may be secured to a user's upper lip U, such that a space 200S between the first and second layers 202, 203 provides a space for the nostrils of the nose.

A fibrous element 205 may be disposed within the space 200S. Each fibrous element may extend through openings 200x extending through the first and second layers 202, 203. A knotted or bulbous portion 205a of the fibrous element 205 may prevent the fibrous element 205 from being removed from the opening 200x and separated from the first and second layers 203, 205. Alternatively, the fibrous element(s) 205 may be secured or glued to the first layer 202 within the space 200S.

The fibrous element 205 may include a plurality of filaments 205b that functionally mimic nose hairs in that they are configured to filter, trap, and/or warm air entering through the space 200S prior to entering into the nostrils of a user when the facial covering 200 is worn. Just as nose hairs function to filter foreign particles and preventing moisture from entering into the nose, so do the filaments 205b. The filaments 205b may be formed from a fabric, cotton, a natural material or other suitable material. Each of the filaments 205b may be a hair-like or string-like member that has a length and a relatively narrow diameter. The filaments 205b may be clustered together to have a density that facilitate trapping substances in the air and/or warming of the air.

Advantageously, the non-rigid, movable nature of the filaments 205b create less of an obstruction for breathing than would a rigid filter such as the filters 110. Since a user who is exerting energy, for example, while running has a greater oxygen need than one would while at rest, it is advantageous that few obstructions to breathing are created while still providing a warming and filtering function.

Figure 4:
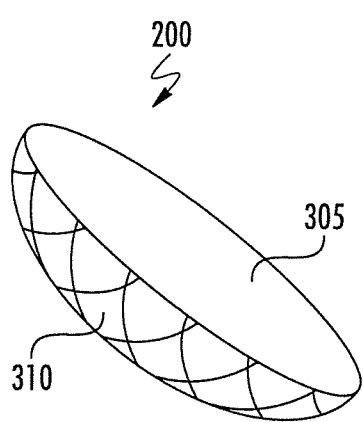
FIG. 4 is a perspective view of another facial protective covering in accordance with a still further embodiment of the present disclosure.

As shown in FIG. 4, a mouth covering 300, may be secured to either the facial covering 100 or 200 or directly to the skin surrounding the mouth by an adhesive, for example. The mouth covering 300 may have a generally conical or ovoid shape such that when placed over the mouth it does not interfere with breathing and/or talking. If material were to be placed directly against the mouth, the movement of the air in and out of the mouth would cause the material to move and would interfere with the breathing and speaking function. Instead, the mouth covering 300 includes a hollow inside 305 to provide a space between the material and the mouth when the covering is placed over the mouth and the outer surface 310 is bowed outward away from the mouth. The outer surface 310 may be formed from a material capable of filtering such as, for example, a cotton or a gauze material.

The filter material of the coverings 100 and 200 may be capable of removing or trapping particulate and/or pathogens from the air. Advantageously, unlike conventional masks which are held in place relative to the air passages (e.g., nasal or mouth) by a friction fitting or tensioning, the coverings 100 and 200 when worn do not move relative the air passages and no gaps exist through which matter (e.g., particulates or pathogens) may pass.

Figure 5:
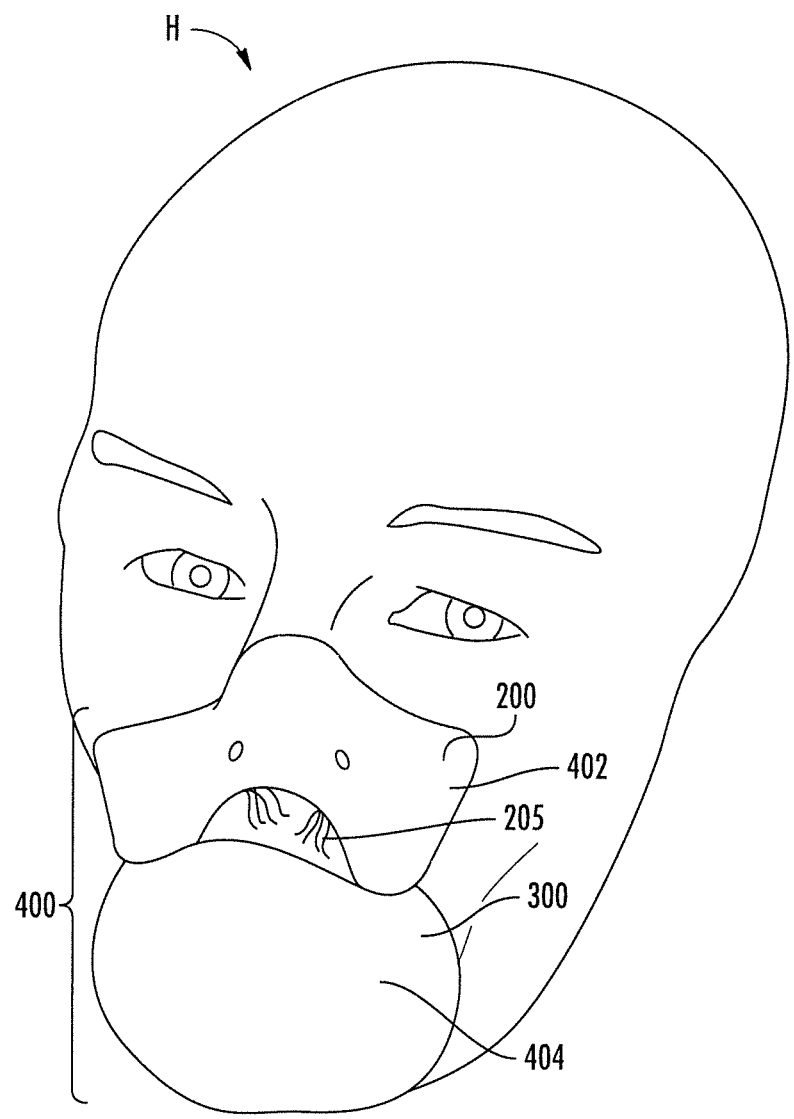
FIG. 5 is a perspective view of a facial protective covering in accordance with another embodiment of the present disclosure.

As shown in FIG. 5, a facial covering 400 may include an upper portion 402 for covering the nose and surrounding facial skin that is similar to the facial covering 100 and a lower portion 404 for covering the mouth and surrounding facial skin such as the chin, for example. The lower portion 404 may be outwardly curved to facilitate breathing and speaking without the material of the lower portion 404 blocking such functions. Optionally, small openings (not shown) may be formed in the lower portion 404 such that some air may pass therethrough to facilitate breathing and speaking while still blocking most air from contacting the skin lying underneath. The upper portion 402 may be substantially similar to the facial covering 200 as described above and the lower portion 404 may be substantially similar to the facial covering 300 described above with the exception that the upper portion 402 and the lower portion 404 may be provided as a monolithic, unitary structure.

Each of the facial coverings 100-400 may include an adhesive backing (not shown) to facilitate securing of the coverings to the skin. When stored, a plastic or paper material may cover the adhesive backing, and when ready to be applied o the skin, the adhesive backing may be exposed by removal of the plastic or paper material. Furthermore, the coverings 100-400 may be configured to be used once and may be disposed thereafter in a similar manner to an adhesive bandage, for example.

Figure 6:
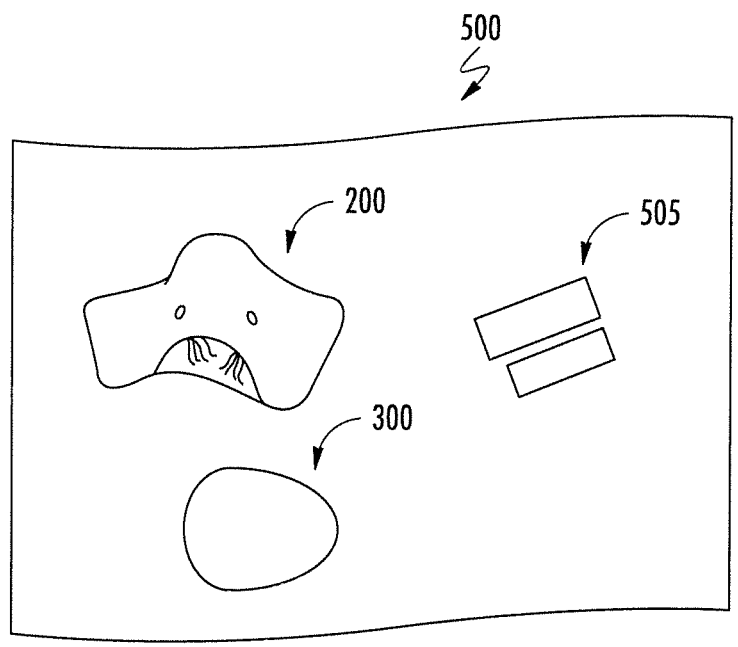
FIG. 6 is a kit shown including the facial protective coverings of FIGS. 3-4 and adhesive tape.

In an embodiment, as shown in FIG. 6, a kit 500 may include at least one of the protective coverings 100-400 (as shown the kit 500 includes protective coverings 200 and 300) and adhesive tape 505, which may be a double-sided tape, for securing the protective coverings to the face of a user. Although shown as including double-sided tape, the kit 500 may additionally or alternatively include any suitable adhesive. Alternatively, the protective coverings 100-400 may themselves include an adhesive backing that is already secured to skin contacting surfaces of the protective coverings 100-400. A material (e.g., paper or plastic) not shown may be releasably secured to the contacting surfaces and when the protective covering(s) are ready to be applied, such material may be peeled or otherwise removed exposing the self-adhering surfaces.

Various means for securing the protective coverings 100-400 may include means other than traditional adhesives such as for example a hydrophilic gel which adheres or sticks to a wearer's skin while also having various skin beneficial properties such as moisturizing and the like.

Having described at least one of the preferred embodiments of the present invention with reference to the accompanying drawings, it is to be understood that such embodiments are merely exemplary and that the invention is not limited to those precise embodiments, and that various changes, modifications, and adaptations may be effected therein by one skilled in the art without departing from the scope or spirit of the invention as defined in the appended claims. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A facial covering configured to be placed on facial skin, comprising:
 a first member comprising:
  an exterior facing surface, the exterior facing surface being unperforated;
  a skin side surface that is configured to be releasably secured in direct contact with and in a sealed relationship with a nasal bridge and ala of nose of a wearer such that an entirety of the skin side surface directly contacts skin surfaces of the nasal bridge and the ala of nose of the wearer with no gap between the skin side surface and the skin surfaces as the skin side surface fits flush against the skin surfaces, the entirety of the skin side surface configured to form an air-tight seal with the nasal bridge and the ala of the nose of the wearer and configured to block air from contacting any of the skin surfaces of the nasal bridge and the ala of the nose when worn, the skin side surface being unperforated;
  a space that is partially defined by an outer edge of the exterior facing surface, the space extending to the outer edge of the exterior facing surface and including a first point that is tangential to an outer edge of the skin side surface and a second point that is tangential to the outer edge of the skin side surface, the first point and the second point being spaced apart from one another on opposing sides of an axis extending lengthwise relative to the nasal bridge when the skin side surface is secured to the nasal bridge, the space being configured to facilitate breathing through nasal air passages when the first member is worn, the outer edge at least partially defining an outermost periphery of the exterior facing surface, the first and second points being along the periphery;
 an adhesive covering an entirety of the skin side surface of the first member; and a filter material disposed within the space, wherein the exterior facing surface of the first member, when worn, is nonoverlapping.

2. The facial covering of claim 1, wherein the filter material is secured to the first member.

3. The facial covering of claim 1, further comprising: a second member that is releasably securable to the first member and being configured to cover the mouth of the wearer.

4. The facial covering of claim 3, wherein the second member includes an adhesive backing.

5. The facial covering of claim 3, wherein the first and second members form a unitary structure.

6. The facial covering of claim 1, wherein the filter material is a fabric.

7. The facial covering of claim 1, wherein the filter material includes filaments that are clustered together to have a density that warms the air and filters substances in the air entering into the space.

8. The facial covering of claim 1, wherein:
the filter material provides a warming and filtering function.

9. The facial covering of claim 8, wherein:
the filter material includes a plurality of filaments that are hair-like and that provide air insulation depending on a humidity of air passing through the plurality of filaments.

10. The facial covering of claim 1, wherein:
the filter material is a fibrous material that includes a plurality of filaments.

11. A kit comprising:
a first member comprising:
an exterior facing surface, the exterior facing surface being unperforated;
a skin side surface that is configured to be releasably secured in direct contact with and in a sealed relationship with a nasal bridge of and ala of nose a wearer such that an entirety of the skin side surface directly contacts skin surfaces of the nasal bridge and the ala of the nose of the wearer with no gap between the skin side surface and the skin surfaces as the skin side surface fits flush against the skin surfaces, the entirety of the skin side surface configured to form an air-tight seal with the nasal bridge and the ala of the nose of the wearer and configured to block air from contacting any of the skin surfaces of the nasal bridge and the ala of the nose when worn, the skin side surface being unperforated;
a space being partially defined by an outer edge of the exterior facing surface, the space extending to the outer edge of the exterior facing surface and including a first point that is tangential to an outer edge of the skin side surface and a second point that is tangential to the outer edge of the skin side surface, the first point and the second point being spaced apart from one another on opposing sides of an axis extending lengthwise relative to the nasal bridge when the skin side surface is secured to the nasal bridge, the space being configured to facilitate breathing through nasal air passages when the first member is worn, the outer edge at least partially defining an outermost periphery of the exterior facing surface, the first and second points being along the periphery;
an adhesive covering an entirety of the skin side surface of the first member; and
a filter material disposed within the space; and
a second member configured to be secured around a mouth of the wear, the second member being outwardly curved,
wherein the exterior facing surface of the first member, when worn, is nonoverlapping.

12. The kit of claim 11, further comprising: a second member that is releasably securable to the first member and being configured to cover the mouth of the wearer.

13. The kit of claim 11, wherein:
the filter material provides a warming and filtering function.

14. The kit of claim 13, wherein:
the filter material includes a plurality of filaments that are hair-like and that provide air insulation depending on a humidity of air passing through the plurality of filaments.

15. The kit of claim 11, wherein:
the filter material is a fibrous material that includes a plurality of filaments.

* * * * *